United States Patent [19]

Umbdenstock

[11] Patent Number: 5,332,579

[45] Date of Patent: * Jul. 26, 1994

[54] NUTRITIONAL SUPPLEMENT FOR OPTIMIZING CELLULAR HEALTH

[76] Inventor: Anthony J. Umbdenstock, c/o Kern Enterprises, Inc., 1081 Whitebridge La, Hanover Park, Ill. 60103-2671

[*] Notice: The portion of the term of this patent subsequent to May 3, 2011 has been disclaimed.

[21] Appl. No.: 979,802

[22] Filed: Nov. 20, 1992

Related U.S. Application Data

[63] Continuation-in-part of Ser. No. 564,131, Aug. 7, 1990, abandoned.

[51] Int. Cl.$^5$ .................. A61K 33/32; A61K 35/78; A61K 33/14; A61K 33/06; A61K 31/555; A61K 31/595; A61K 31/355; A61K 31/34; A61K 31/195; A61K 31/07

[52] U.S. Cl. .................. 424/639; 424/195.1; 424/641; 424/643; 424/655; 424/678; 424/681; 424/682; 514/168; 514/188; 514/458; 514/474; 514/566; 514/725; 514/810; 514/812; 514/813.

[58] Field of Search .................. 424/195.1, 630, 639, 424/641, 643, 681, 678, 682, 655; 514/276, 355, 356, 392, 566, 725, 168, 188, 458, 474, 810, 812, 813

[56] References Cited

U.S. PATENT DOCUMENTS

| | | | |
|---|---|---|---|
| 3,989,823 | 11/1976 | Di Costanzo | 424/195.1 |
| 4,761,429 | 8/1988 | Blum et al. | 514/561 |
| 4,973,467 | 11/1990 | Sahley | 424/195.1 |

FOREIGN PATENT DOCUMENTS 2922670 12/1980 Fed. Rep. of Germany.
8203551 10/1982 PCT Int'l Appl..

OTHER PUBLICATIONS

The Merck Index, 10th Edition (1983), p. 9705, Citation No. 9709.
The Merck Manual, 14th Edition (1982), pp. 1415–1420.
Joan Matthews Larson, Ph.D., "Alcoholism–The Biochemical Connection," 1992, pp. 1–45.
Alcohol Health & Research World, "Alcohol and Nutrition," vol. 13, No. 3 (1989), pp. 196–217.
Phillips, M. D., et al., "Pathogenesis of Fetal Alcohol Syndrome," vol. 13, No. 3 (1989), pp. 219–267.
Alcohol Health & Research World, "Alcohol and the Brain," vol. 14, No. 2 (1990), pp. 85–143.
Seelig, M. D., "Magnesium Deficiency in the Pathogenesis of Disease, Early Roots of Cardiovascular, Skeletal, and Renal Abnormalities," 1980.
Albert Szent-Györgyi, "Bioelectronics–A Study in Cellular Regulations, Defense, and Cancer," Academic Press, 1968.
John J. Miller, Ph.D., "Alcoholism–A World-Wide Problem." (1980).
John Hathcock, Ph.D., "Vitamin Safety Index," Pharmacy Times, 1985.
Garrison et al., The Nutrition Desk Reference (1985) pp. 116–124 and 220–226.
Guenther, R. M., "The Role of Nutritional Therapy in Alcoholism Treatment", The International Journal of Biosocial Research, vol. 4, No. 1, pp. 5–18 (1983).

Primary Examiner—Frederick E. Waddell
Assistant Examiner—Raymond J. Henley, III
Attorney, Agent, or Firm—Welsh & Katz, Ltd.

[57] ABSTRACT

A nutritional supplement, functioning as a food for special dietary use, enhances diets and assists persons recovering from addiction to health damaging substances. Since cellular damage and deficiencies occur and continue to exist even after the person has stopped abusing the substances, use of the nutritional supplement, which contains a variety of minerals, vitamins, herbs, amino acids, and other substances and nutrients, should be continuous. The nutritional supplement consists of a mixture of nutrients which cooperate synergistically in enhancing cellular metabolic pathways and assists in normalization of cellular functions and optimization of cellular health.

10 Claims, 1 Drawing Sheet

NUTRITIONAL SUPPLEMENT FOR OPTIMIZING CELLULAR HEALTH

This application is a continuation-in-part of Ser. No. 07/564,131, filed Aug. 7, 1990, now abandoned.

BACKGROUND OF THE INVENTION

This invention relates to a nutritional supplement, which assists a person addicted to alcohol, drugs, tobacco, sugar or the like in recovery from such an addiction.

Field of the Invention

It is known that some humans may abuse substances such as alcohol, marijuana, cocaine, heroin, tobacco, or other substances. It is also known that abuse of such substances results in humans having compulsive disorders, which include but are not limited to alcoholism, addictions to marijuana, tobacco, cocaine, heroin, caffeine, sugar, or the like. These compulsive disorders cause changes in the metabolism of human cells in such a way that metabolic voids or errors in metabolism occur. These cellular changes produce an addictive state which expresses itself as the compulsive disorder. This compulsion is created by the cellular changes which makes the human crave the addictive substance. Thus, substance abuse results in adverse cellular metabolism which compromises health in the human addict.

Substance abuse affects cellular metabolism throughout the human body. The human liver is generally one of the first organs affected. This is especially important because the liver is a highly active, vital organ which has been termed the "metabolic capital" of the body, performing over 400 essential bodily functions. For example, the liver performs bile synthesis and secretion needed for fatty acid metabolism, while the liver's vascular network and specialized cells filter and store blood. The liver also contributes to carbohydrate metabolism for conversion of galactose and fructose to glucose, conversion of amino acid residues to glucose in gluconeogenesis, formation and storage of glycogen in glycogenesis and the formation of many important chemical compounds from carbohydrate intermediates. The liver further performs fat metabolism which includes fat conversion to transport form—the formation of lipoproteins; oxidation of fatty acids to acetoacetic acid, then to acetylcoenzyme A(CoA) and into the citric acid cycle to yield energy; formation of bile salts, cholesterol and phospholipids; and conversion of carbohydrate and protein intermediates to fat through lipogenesis. The liver still further performs protein metabolism which occurs via deamination of amino acids; production of lipotrophic factors for fat conversion to lipoproteins; formation of plasma proteins; urea formation for removal of ammonia from body fluids; and many amino acid interconversions, transamination and amination and synthesis of nonessential amino acids, purines, pyrimidines, creatine, phosphate et al. Other related functions of the liver include storage of Vitamins A, D, B12 and other B complex Vitamins as well as Vitamin K; production of blood coagulation factors from prothrombin in the presence of Vitamin K, and from other blood factors such as fibrinogen, accelerator globulin, and factor VII; storage of iron as ferritin; conjugation and excretion of steroid hormones; and detoxification of certain drugs including morphine and barbiturates.

As a result of substance abuse, these functions of the liver operate at a less than optimal level and possibly less than maintenance level. If the substance abuse is prolonged or severe, such ailments as cirrhosis of the liver may occur.

The next major organ affected by substance abuse is the brain, which consists of tens of billions of cells that perform thousands of functions. The human brain is the central organ for coordination and regulation of the human body which controls speech, locomotion, behavior and a broad range of intellectual and emotional functions. Unlike other human organs, the brain cannot regenerate a cell once destroyed. The brain however, if properly nurtured, can repair compromised brain cells, where, for example, compromised brain cells may result from intoxication. In alcohol abuse many of the brain structures are so eroded by the solvent effect of alcohol that brains of alcoholics are not used in cadaver labs to study brain structures.

If a human is abusing alcohol, cells within the liver and brain may be damaged. For example, alcohol abuse causes cellular damage to the brain and liver due to the effects of ethanol and acetaldehyde build up in the tissues. Ethanol is broken down by the enzyme alcohol dehydrogenase to acetaldehyde. This degradation process is started in the liver. When acetaldehyde dehydrogenase is depleted, a rapid build up of acetaldehyde occurs, which is capable of producing THIQ (tetrahydroisoquinoline) a false neurotransmitter that interferes with thought processes. Toxification of specific enzyme systems occurs when nutrient deficits at the cellular level permits the beginning of destructive cellular changes. Destructive cellular changes alter cell functions in ways that eventually lead to more frequent use and greater quantities of the addictive substance(s) resulting in a psychological and/or physical dependency.

Although Alcoholics Anonymous and other programs treat the addiction, they do not address the physical changes on the cellular level. Such programs may do a very good job of addressing many of the addict's social, spiritual and some of the psychological reasons for the addiction. Cellular deficits of nutrients are not discussed nor addressed by the programs nor by other methods of counseling.

Treatments for alcoholics, drug addicts, smokers and/or like persons addicted to harmful substances have heretofore included relatively large dosages of Vitamins such as Vitamin B1, Niacin, L-Glutamine or other factors individually or in combinations of one or two items at relatively high dosages. In these treatments, the nutrients are used as if the cells were deficient in only one or a few nutrients. When deficiencies occur, they generally occur in many areas simultaneously. Excessive use of one or more nutrients may alter cellular biochemistry in some undesirable ways that overwhelm or compromise the benefits. These treatments fail to normalize and optimize metabolic pathways in the addictive individual because they address only a portion of the cellular metabolic needs, often at the expense of others. While it is known that the addict relies on the addictive substance(s) as a substitute for a nutritional diet and soon experiences losses in healthy cells especially in the brain, lung, liver and/or pancreas it must be recognized that withdrawal from the addictire substance(s) requires the opening up of normal metabolic pathways to the vital organs in a manner that will biochemically build up the damaged cells of the brain, liver, adrenal, kidneys, pancreas and/or other organ tissues.

Cellular deficiency of a substance abuser has been addressed to a very limited degree. For example, some nutritional therapies have been developed to address one or more nutritional deficits. Alkonil was a product utilizing niacin, Vitamin C and glutamine at a dose of one gram each per tablet. Although this produced benefits in the alcoholic, it addressed too few of the metabolic compromises in the addict to be truly effective. For example, minerals and B Vitamin needs are not addressed, leaving a constellation of nutritional deficits in the addict.

Standard medical procedures usually treat one or more signs or symptoms of alcoholism during crisis. Such treatments may include use of intravenous magnesium for delirium tremens; or treat the early stages of cirrhosis of the liver with drugs. This type of treatment does not address the cellular deterioration as happens to the Ito cells of the liver which become fat storage depots. Many of these treatments are useful in crisis intervention and addressing the effects of substance abuse, yet do little to treat the cause of substance abuse or restore normal cellular metabolism.

Therefore, a need exists for a comprehensive nutritional supplement that effectively treats both the general and specific nutrient cellular deficits and subcellular nutritional requirements for normalization and optimization of health at the cell level first, and eventually the health of the whole organism itself—the human addict.

SUMMARY OF THE INVENTION

The cellular needs discussed above and others are substantially met by the nutritional supplement of this invention, that is a nutritional supplement for special dietary use. The nutritional supplement of this invention, which assists a human organism with a cellular metabolic deficiency, is comprised of appropriate amounts of nutrients for the repair and normalization of the cells and cellular pathways of the human body to thereby return the body to a normal or substantially normal operation.

The functioning of the nutritional supplement in this invention is further elucidated in three drawings as follows:

BEST MODE FOR CARRYING OUT THE INVENTION

Figure 1:
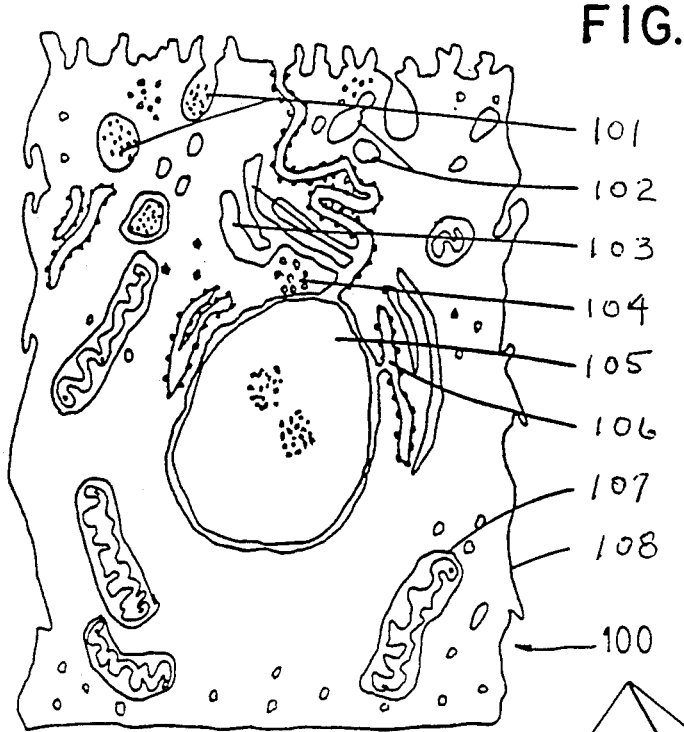
FIG. 1 illustrates the basic content of a typical human cell.

FIG. 1 illustrates an elementary diagram of a typical human cell (100). the typical human cell (100) comprises a plurality of secretion vacuoles (101), a plurality of lipid droplets (102), a plurality of golgi apparatus (103), a plurality of centriole (104), a nucleus (105), at least one endoplasmic reticulum (106), a plurality of mitochondrion (107), and at least one plasma membrane (108). Regardless of which organ the cell is part of, each cell has the basic structure of FIG. 1 and has generally similar nutritional needs. For example, cells (100) obtain nutrients from fluid between the cells via the mitochondria (107). The mitochondria (107) extract energy from nutrients and treat the energy released by oxidative processes and the simultaneous formation of the high-energy chemical bonds of ATP (adenosine triphosphatase). The nucleus (105) is characterized by its high content of chromatin, which contains most of the cellular DNA (deoxyribonucleic acid). The golgi apparatus (103) produces and maintains their internal membrane—the endoplasmic reticulum (106). Closely associated with the inner surface of the endoplasmic reticulum (106) are numerous granules rich in RNA (ribonucleic acid) termed ribosomes (not shown)—the site of protein synthesis within the cell. The reticular system is most highly developed in the liver and pancreas where cells (100) are actively engaged in the production of proteins. Lysosomes (not shown) are subcellular organelles which contain digestive enzymes that break down fats, proteins, nucleic acids and other large molecules into smaller molecules capable of being metabolized by the enzyme systems of the mitochondria (107). The health of the lysosome depends on the lipoprotein membrane (108) remaining intact. Once the membrane is ruptured by, or is in the presence of a solvent, such as alcohol, release of lysosomal enzymes is quickly followed by dissolution (lysis or death) of the cell.

Figure 2:
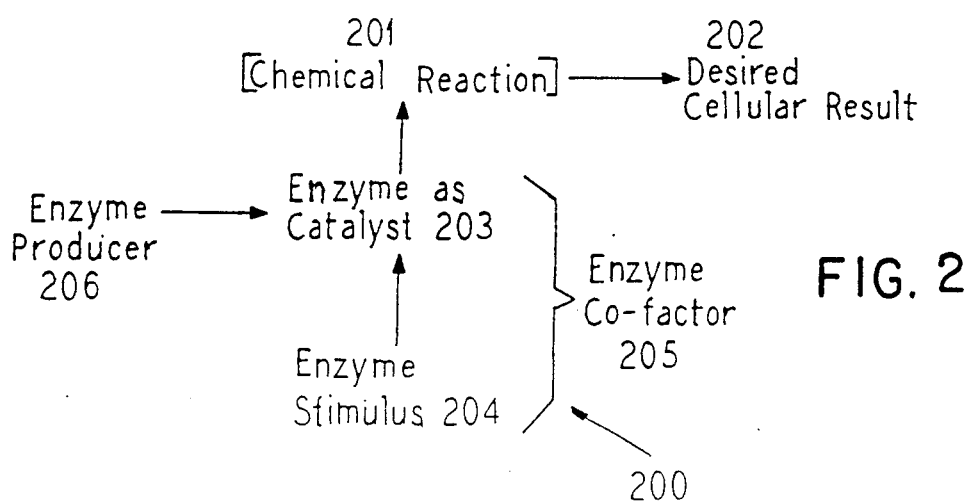
FIG. 2 illustrates a typical cellular chemical reaction.

FIG. 2 illustrates a schematic representation of cellular metabolism (200) that occurs at the cellular and subcellular levels in a human. The cellular metabolism (200) comprises a chemical reaction (201) which produces a desired cellular result (202).

For the chemical reaction (201) to efficiently occur, at least one enzyme (203) which acts as a catalyst for the chemical reaction (201) must be present. However, for proper enzyme catalysis, at least one enzyme stimulus (204) and at least one enzyme co-factor (205) must also be present. The enzyme stimulus (204) stimulates enzyme catalysis, while the enzyme co-factor regulates the chemical reaction (201) at an approximately normal metabolic rate. The cellular metabolism (200) may further comprise an enzyme producer (206) that produces enzymes (203). As an example, a healthy metabolic reaction (200) may comprise a chemical reaction (201) of combining magnesium, glutamic acid, and NH4 to produce the desired cellular result (202) of glutamine and NH3. NH3 can be disposed of via the urinary tract after it is picked up in the portal circulatory system and deposited in the kidney. This process is a major detoxifier of protein residue that otherwise accumulates in the liver and other tissues. During incomplete breakdown of proteins, free ammonia (NH4) can build up in tissue, causing further cellular damage.

Figure 3:
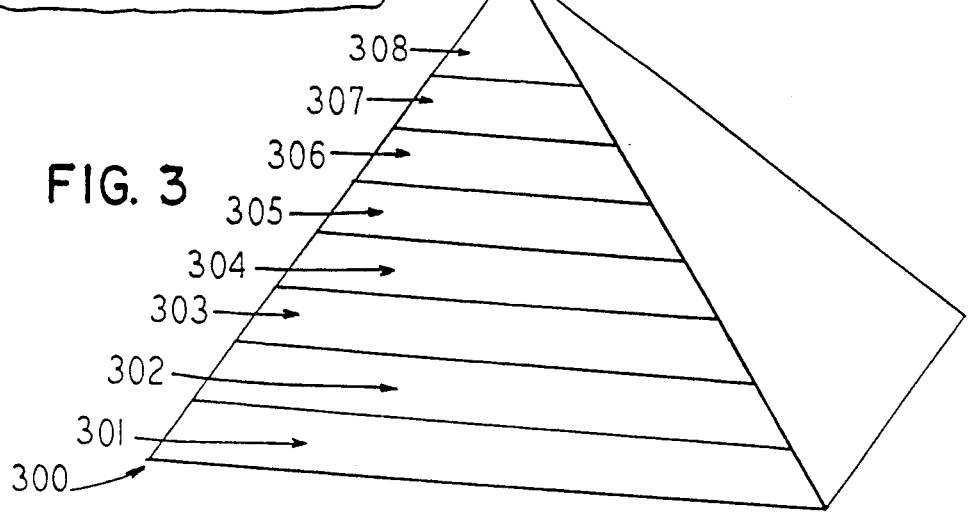
FIG. 3 illustrates cellular metabolism in humans.

As can be seen in FIG. 3, the pyramid of cellular metabolism in human (300), it is important to note that both diet and environment (301) influence enzymes (302), intermediary metabolites (303), hormones (304), biochemistry (305) and performance (306) sequentially before symptoms (307) or signs (308) become obvious. An important fact at this point is that although signs (308) and symptoms (307) are the bedrock of differential diagnosis with either invasive organisms (infective disease) or trauma (injury), contemporary medicine is not designed to deal effectively with cellular metabolic change.

Tragically, patients are often dismissed as neurotic when they complain of multiple and non-specific symptoms or signs. However, once a physician is able to change perspective and views the individual from the cellular level up, the symptoms and signs are confirmation of cellular metabolic changes which will affect performance. A healthy liver cell, for example, has more than 400 functions to perform. If the liver becomes compromised or if utilization of abundant nutrient is not immediately available, then liver function suffers and eventually the patient suffers. This condition is intensified by the ravages of addiction.

Much the same can be said for the adrenal gland where adrenalin permits a person to respond to emergencies and the mineralocorticoids are important factors in maintaining normal cellular function. Whenever a person is under physical or psychological stress the adrenal glands get a heavy work-out. In addition, the glands are overwhelmed allowing fatigue to set in and a wide variety of symptoms to appear.

The brain, on the other hand, along with the eyes represents about 2% of a person's body weight, yet require over 25% of daily body nutrition. Glucose is the body sugar used as a primary brain fuel and is consumed continuously. Of great importance are two other fuels which are oxidized in the brain, namely niacin/niacinamide and glutamic acid. Niacin/niacinamide is the building block of NAD, NADH, NADPH, and niacinamide bridge reactions necessary for normal brain metabolism. Glutamic acid arrives at the blood/brain barrier as glutamine where it loses an amine, becoming glutamic acid on entering the brain. These are important fuels that some therapists used in megadoses with alcoholics and drug addicts. Although these megadoses have often proved useful, they both address too few of the cellular metabolic weaknesses involved and require much larger doses than would be necessary if most or all the metabolic needs were addressed.

In an addict, the abused substance(s) affect the enzymes, hormones and biochemistry of the cell. These affects can be observed by changes in performance. For example, in catalysis of an enzyme (see drawing 2), it is critical to have adequate supplies of enzyme stimuli (204) and enzyme co-factors (205) and other nutrient substrates for normal metabolism to occur. When alcohol or drugs are abused, many of these nutritional substances are used up in attempting to neutralize the abused substance, thus leaving a deficit of nutrients at the cell level for normal metabolism. In time, these subclinical deficits alter metabolism in such a way that cravings occur which foster further abuse of the substance which, in turn, is needed more and more frequently.

When alcohol is the abused substance, certain metabolic and adverse metabolic processes take over so that even normal food material and sufficient sugar permit the body to produce its own alcohol. This unhappy situation further aggravates the recovery process by causing the patient to relapse in an otherwise healthy rehabilitation program. For example, if the person is addicted to beer—the hops, barley or other grains ingested, along with several teaspoons of sugar—can set off a cellular reaction similar to the consumption of beer itself. The same is true for rye whiskey, where rye bread and sugar—in coffee or sugared soda—can trigger an extreme craving for rye whiskey even though it would appear that the recovery process is proceeding normally.

Thus, the nutritional supplement comprises at least one enzyme activating substance and at least one enzyme co-factor. The enzyme activating substance, which may be a mineral such as magnesium, is supplied in sufficient amounts to supplement the dietary input such that normalizing some of the enzyme systems begins. For example, reconstitution of ATP (adenosine triphosphatase) from ADP (adenosine diphosphate) is a magnesium dependent process which can readily restore itself as long as sufficient magnesium exists at the cell level. The RDA (recommended dietary allowance) for magnesium is 400 mg in the adult. A good American diet supplies about 250 to 300 mg per day. It will further take at least 200 to 400 mg of magnesium in supplemental form to overcome the loss traceable to the abused substance.

There is no danger of magnesium overdose since the minimum toxic dose of magnesium, with the exception of kidney failure or the like, is generally accepted to be 12,000 mg per day. Doses in high ranges, however, reduce the body's absorption of the nutrient. It is important, therefore, to supply magnesium at a more reasonable dose to optimize function at the cell level.

The enzyme co-factor, which is a Vitamin, such as thiamine (Vitamin B1) and pyridoxine (Vitamin B6), is needed in sufficient amounts along with magnesium to normalize specific enzymes. For example, thiamine is a co-factor with magnesium in controlling the rate of lipogenesis (cellular fat generation). There is usually an increase of lipid (fat) and cholesterol in the liver and kidney of magnesium and thiamine deficient rats. The hypothesis is that the lipogenic pathways are activated by blockage of the enzyme pathway to the citric acid cycle.

Of special interest in treating alcoholism, thiamine and magnesium appear to be factors in acetaldehyde accumulation from use of alcohol via the thiamine dependent step in the metabolic pathway where acetaldehyde goes to pyruvate (6). Supplementation of thiamine along with magnesium permits more normal cellular metabolism of these and other such enzyme activities allowing an approximately normal metabolic rate to be re-established over a relatively short period (30 to 90 days minimum). After an initial period of moderate supply of these nutrients, the intake can be reduced while still maintaining fairly efficient cellular enzyme functions. Thiamine is also a factor in carbohydrate and glucose metabolism which further assists in reducing the sugar cravings of many addicts.

The nutritional supplement may further comprise an enzyme producer such as an amino acid like glutamic acid. Glutamic acid is a substrate used along with magnesium and the by-product of protein catabolism NH4 to produce NH3 and glutamine. NH3 is the reduced ammonia form which is readily disposed of via urine while NH4 is free ammonia which can toxify or harm normal metabolism. The incomplete breakdown of proteins which produces NH4 is often increased by substance abuse. Glutamic acid is one of the three oxidizable brain fuels along with glucose and niacin/niacinamide. Thus a supply of glutamic acid, an amino acid, provides a catalyst for at least part of the cellular chemical reaction which permits degradation of harmful NH4 to NH3 for removal via urine.

The nutritional supplement should also comprise an herbal antispasmodic substance, such as Valerian root, in sufficient amounts to normalize the nutritional substrates of the neuronal pathways permitting the human organism to normalize at least one of the sub-cellular ligand binders or cementous aspects of normal cells allowing these metabolic functions to become more normal. There are many other aspects of normalization of metabolic factors and nutritional substrates beyond ligand binders and various sub-cellular cementous substances including collagen formation and utilization of cholesterol in the white matter of the brain and inside the nerve sheath along with cellular bioelectric factors.

The enzyme co-factor of the nutritional supplement should comprise water soluble Vitamins such as B Vitamins which contribute to normalize cellular metabolic rates. The B Vitamins permit completion of the enzyme reaction once it is activated by a specific mineral. For example, niacin as NADH is reduced to NAD. Fat soluble Vitamins include the antioxidant Vitamins A, D and E which assist in control of the rate of burning of the enzyme. If an enzyme burns or oxidizes too rapidly, less cellular work is accomplished and free radical pathology may be promoted. For example, Vitamin A is a factor in the collagen synthesis of the Ito cells in the liver. When Vitamin A levels are reduced in the Ito cells by ethanol, the cells are changed to fat storage depots in the early stages of liver cirrhosis. When Vitamin A deficiency occurs in the liver then fibrosis can no longer be controlled, which adds to existing free radical pathology.

The enzyme activating substance should be magnesium which activates more than 70% of the enzymes in the human organism (8) including production and transfer of energy, muscle contraction, protein synthesis and nerve excitability. Alcohol and other drugs reduce the amount of magnesium available for normal metabolism as some is diverted for detoxification and degradation of these substances within cells.

The enzyme activating substance should also comprise zinc which encourages complete protein digestion by activating thiol and carboxyl proteases. Alcohol abuse interferes with normal protein digestion. Incomplete breakdown of proteins in turn allows free radical damage to the cell. The nutritional supplement may also contain chromium which, in conjunction with manganese, encourages complete and functional carbohydrate metabolism. Normalization and control of blood sugar levels are partially dependent on the functions of manganese and chromium in carbohydrate metabolism.

The nutritional supplement should still further comprise Vitamin C which is a factor in the structure and function of collagen tissue and is also part of the fibrin net necessary for healthy cardiac muscle tissue. One of the first structures to disappear in compromised cardiac muscle is the fibrin net. It is important to note that while the level of Vitamin C is higher than the RDA, it is necessary to fulfill the increased requirements of the addict, and does not approach the so called megadose range.

Thenutritional supplement or substance addiction recovery supplement is used in recovering from the cellular damage caused by the addictive process. The addicting substance(s), whether alcohol, drugs, tobacco, or other substances, actively uses up various nutritional factors such as nutritional substrates supplied by an herb; amino acids supplied by glutamic acid or other amino forms; chelated magnesium, zinc, manganese, chromium or other minerals (these minerals may be chelated with glycine or other organic amino compounds); thiamine, pyridoxine or other water soluble B Vitamins; Vitamin A or other fat soluble Vitamins; Vitamin C as a component of healthy collagen or other tissue; choline that is a lipotrophic factor improving fatty acid metabolism and inositol to maintain availability of the substrate muscle sugar in the compromised tissue of an addict. The substance addition recovery supplement or nutritional supplement is needed to re-supply these nutrients in addition to those available in the diet. This abundance, but not a megadose, is necessary to help normalize cellular function and metabolic pathways by providing a ready source of nutrients to an otherwise compromised organism, first the damaged cells then the human addict.

The cravings associated with addictions appear to be a generalized response of the organism which has developed one or more of the nutritional deficiencies associated with addictire states. These cravings are addressed in the substance addiction recovery supplement or nutritional supplement by supplying at least one enzyme activating substance, which may be the mineral magnesium; and at least one enzyme co-factor, which should be Vitamin B1 and B6; Vitamin B12 and folic acid is also necessary. The nutritional supplement may also comprise any or all of the following, nevertheless the best mode contemplates using at least the following as a minimum treatment; at least one amino acid; Vitamin C for normalization of collagen tissue and the fibrin net of cardiac muscle as structural components and other cellular functions; other substances found necessary to restore the body cellular functions to normal are Vitamin A, beta-carotene, niacin/niacinamide, Vitamin C, zinc, and valerian root.

When the nutritional components, minerals, Vitamins, amino acids, and herbs as set forth above, are supplied to an addict, the human body is able to resume a more normal cellular biochemical function, decreasing the need for the addictive substance(s). This combination of substances for special dietary use is necessary to address the nutritional deficiencies and/or errors of metabolism created by the use and/or abuse of an addictive substance.

A synergistic group of nutrients can be successfully assembled to supply the basic cellular needs in specific or generalized deficiency conditions. In addictire states there are a number of areas that must be addressed in order to provide a food for special dietary use that answers cellular needs and permits normalization or optimal nutrition. When such a group of nutrients are made available to the cells, an optimum effect occurs, wherein the whole can be greater than the sum of the parts. In this instance no individual nutrient generally meets the cellular needs of the addictive individual as effectively as the synergistic aspects of the above combination of substances. The effects can be enhanced by using all of the elements mentioned above taken as a nutritional supplement. This synergistic combination of nutrients includes, but is not necessarily limited to, specific chelated minerals with their Vitamin co-factors such as chelated magnesium (such as magnesium glycinate) with Vitamins B1, B2, B6, niacin/niacinamide, B12, folic acid, biotin and pantothenic acid; chelated zinc (such as zinc glycinate) for specific liver enzyme factors; chelated manganese (such as manganese glycinate) and/or chromium (such as chromium glycinate) for carbohydrate metabolism; Vitamins A, D (as Vitamin $D_3$), and E as fat soluble Vitamins and antioxidants; Vitamin C as an aspect of structural integrity of collagen and other cellular structural and functional requirements; glutamine and/or glutamic acid with chelated magnesium (for the degradation of $NH_4$ to $NH_3$ and glutamine) for detoxification of free ammonia at the cell level; nervine and/or antispasmodic herbs such as valerian root or other herbs to nourish, normalize and optimize the nutritional substrates and neuronal pathways.

Through this invention, nutrients, balanced synergistically with each other, are provided to effect beneficial changes at the cellular level. These changes will optimize healthy cellular functions for the addict, thus lessening the need and/or desire for the addictive substance(s).

When using a specific group of nutrients, as in this invention, it is imperative to note the optimal nutrient contents of the assembled nutrients and to understand their synergistic nature. Thus, the combination of nutrients combine for an effect where the combination is greater than any individual nutrient. There is an effective range for each of the individual nutrients used in this invention with a specific level chosen to foster the optimum interaction of all of the parts, thus forming a synergistic complex which is capable of producing an optimum effect which will result in an overall reduction of craving for the addictive substance(s).

Since the addictive process is not identical for all individuals, the substances supplied by the subject invention is designed to supply the needed nutrients for normalizing cellular metabolic pathways in the greatest number of individuals with minimal cost to the patient. This product is further designed to be used in conjunction with existing alcohol and/or drug treatment programs to increase their effectiveness and to decrease recidivism or the rate of relapse. The nutritional supplements of the subject invention should be different for each addiction. However, regardless of the addiction, there are some primary nutrients necessary in all cases, while others are supportive and specialized for each different addiction. Vitamins C and A, Beta Carotene, niacin, niacinamide, and the herb Valerian Root may be found in all formulas. The smoking cessation supplement should comprise higher levels of Vitamins c and e, selenium, zinc, and may include minerals such as cooper and calcium while adding the herb Echinachea and possibly others. The supplement for alcohol treatment programs should comprise higher levels of magnesium, Vitamins B1, B6, B12, and folic acid; minerals maganese, chromium; the amino forms glutamic acid and glutamine with perhaps others.

Other specialized supplements for assisting in food addictions such as with sugar, chocolate, or salt, may have different levels of magnesium, chromium, manganese, zinc, and Vitamins A and C but will not be limited to these changes as additional herbs, amino forms, or other Vitamins and minerals may be useful in this supplement.

| PRIMARY NUTRIENTS | Low | High | Optimum |
| --- | --- | --- | --- |
| Magnesium | 50 mg | 1000 mg | 150 mg |
| Zinc | 10 mg | 100 mg | 30 mg |
| Vitamin A | 1000 IU | 15000 IU | 4500 IU |
| Beta Carotene | 5000 IU | 45000 IU | 15000 IU |
| Vitamin C | 100 mg | 10000 mg | 60 mg |
| Vitamin B1 | 10 mg | 300 mg | 100 mg |
| Vitamin B6 | 50 mg | 1000 mg | 150 mg |
| Vitamin B12 | 30 mcg | 300 mcg | 90 mcg |
| Niacin | 10 mg | 500 mg | 60 mg |
| Niacinamide | 100 mg | 2000 mg | 300 mg |
| Valerian Root | 50 mg | 1000 mg | 150 mg |

| SECONDARY NUTRIENTS | | | |
| --- | --- | --- | --- |
| Calcium | 100 mg | 5000 mg | 500 mg |
| Chromium | 20 mcg | 500 mcg | 60 mcg |
| Copper | 1 mg | 20 mg | 5 mg |
| Iron | 5 mg | 100 mg | 20 mg |
| Manganese | 5 mg | 100 mg | 15 mg |
| Selenium | 20 mcg | 400 mcg | 200 mcg |
| Vitamin D3 | 100 IU | 1000 IU | 300 IU |
| Vitamin E | 10 mg | 800 mg | 30 mg |
| Vitamin B2 | 5 mg | 100 mg | 30 mg |
| Biotin | 100 mcg | 1000 mcg | 300 mcg |
| Pantothenic Acid | 50 mg | 500 mg | 150 mg |
| Choline | 50 mg | 900 mg | 300 mg |
| Inositol | 100 mg | 1000 mg | 300 mg |
| Glutamic acid | 50 mg | 1000 mg | 150 mg |
| Glutamine | 50 mg | 1000 mg | 150 mg |
| Echinachea | 50 mg | 1000 mg | 150 mg |

Other amino forms such as alanine, arginine, aspartic acid, asparagine, cystine, cysteine, cystathionine, glycine, histidine, isoleucine, leucine, lysine, methionine, proline, phenylalanine, serine, threonine, tryptophan, valine or others, may be used.

Other herbs such as comfrey, catnip, cayene, dong quai, walnut, black cohosh, wood betony, kava kava, ginger, gota kola, garlic, ginsing, slippery elm, skullcap or others, may be used.

Other minerals may be used, such as potassium, boron, molybdenum, lithium, iodine, germanium, rubidium, silicon, and vanadium.

Possible minor modifications of nutrient levels or minor additions or deletions may be made in individual cases as may prove more beneficial in approaching the nutritional optimum under clinical and/or research conditions. The optimal dosage for bringing the cell to viability in the shortest time period is contemplated to be orally ingested daily for at least 90 days and possibly longer, with a maintenance dose comprising the lower dosage set forth on a daily basis. The biochemical individuality of a given addict may require the highest dose (set forth) for an initial period of 10 to 90 days; or may require only minimal treatment.

While the above formulation is optimal in most circumstances in aiding recovery from addictive conditions, it is possible with a different formulation, to achieve some success in more limited circumstances and with less dramatic success.

The following examples are indicative of optimal formulations for smoking, alcoholism, and the various food addictions. Each example includes all of the primary nutrients set forth above with only the dosage changes indicated.

| SMOKING ADDICTION Primary nutrients with the following differences: | |
| --- | --- |
| Zn | 60 mg |
| Copper | 6 mg |
| Se | 200 mg |
| Higher Vitamin C | 1000 mg |
| Biotin | 400 mcg |
| Vitamin D | 400 IU |
| Vitamin E | 60 mg |
| Echinachea | 200–300 mg |

| ALCOHOL ADDICTION Primary nutrients with the following differences: | |
| --- | --- |
| Mg | 300 mg |
| B6 | 300 mg |
| Cr | 60 mcg |
| Mn | 15 mg |
| Vitamin D3 | 300 IU |
| Choline | 150 mg |
| Inositol | 300 mg |
| Pantothenic | 150 mg |

-continued

ALCOHOL ADDICTION
Primary nutrients with the following differences:

| Acid | |
|---|---|
| Glutamic Acid | 210 mg |
| Glutamine | 150 mg |

SWEETS AND JUNK FOOD ADDICTION
Primary nutrients with the following differences:

| Zn | 15 mg |
|---|---|
| Vitamin A | 1500 IU |
| B1 | 30 mg |
| B12 | 30 mcg |
| Niacin | 30 mg |
| Niacinamide | 150 mg |
| Lower | |
| Cr | 60 mcg |
| Mn | 15 mg |
| Vitamin E | 30 mg |
| B2 | 15 mg |
| Biotin | 100 mcg |
| Pantothenic Acid | 60 mg |
| Glutamic Acid | 150 mg |
| Glutamine | 150 mg |
| Echinachea | 150 mg |

While the invention has been described with reference to a preferred embodiment, it will be understood by those skilled in the art that various changes may be made and equivalents may be substituted for elements thereof without department from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

I claim:

1. A method for aiding in the recovery of addicts by the oral administration of a nutritional supplement for utilization by cells to reestablish normal cellular biochemistry comprising the step of orally administering a supplement comprising the following elements on a daily basis for at least 30 days:
   About 1500 IU to about 15000 IU Vitamin A;
   About 5000 IU to about 45000 IU Beta-carotene;
   About 33 mg to about 300 mg Vitamin B1;
   About 50 mg to about 1000 mg Vitamin B6;
   About 30 mcg to about 300 mcg Vitamin B12;
   About 20 mg to about 500 mg Niacin;
   About 100 mg to about 2000 mg Niacinamide;
   At least about 100 mg Vitamin C;
   About 5 mg to about 100 mg Magnesium;
   About 10 mg to about 100 mg Zinc;
   About 50 to about 1000 mg Valerian Root;
   At least two additional minerals selected from the group of calcium, chromium, copper, iron, manganese, and selenium; and
   At least four additional Vitamins, herbs, and amino acids selected from the group consisting of Vitamin D3, Vitamin E, Vitamin B2, biotin, pantothenic acid, choline, inositol, glutamic acid, glutamine, and echinachea.

2. The method of claim 1 wherein the supplement includes about 100–1000 IU of Vitamin $D_3$.

3. The method of claim 1 wherein the supplement includes about 10–800 mg of Vitamin E.

4. The method of claim 1 wherein the supplement includes about 5–100 mg of Vitamin B2.

5. The method of claim 1 wherein the supplement includes about 100–1000 mcg of Biotin.

6. The method of claim 1 wherein the supplement includes about 50–500 mg of Pantothenic Acid.

7. The method of claim 1 wherein the supplement includes about 70–900 mg of Choline.

8. The method of claim 1 wherein the supplement includes about 100–1000 mg of Inositol.

9. The method of claim 1 wherein the supplement includes about 50–1000 mg of Glutamic Acid and 50–1000 mg of Glutamine.

10. The method of claim 1 wherein the supplement includes about 50–1000 mg Manganese and about 20–500 mcg Chromium.

* * * * *

UNITED STATES PATENT AND TRADEMARK OFFICE
CERTIFICATE OF CORRECTION

PATENT NO. : 5,332,579
DATED : July 26, 1994
INVENTOR(S) : Anthony J. Umbdenstock It is certified that error appears in the above-indentified patent and that said Letters Patent is hereby corrected as shown below:

Column 2, line 64, "addictire" should be "addictive".
Column 3, line 55, "the" should be "The".
Column 7, line 48, "Thenutritional" should be "The nutritional".
Column 8, line 7, "addictire" should be "addictive".
Column 8, line 12, "is" should be "are"
Column 8, line 34, "addictire" should be addictive".
Column 9, line 31, "c and e" should be "C and E"
Column 11, line 44, insert "addicted to a substance selected from the group consisting of marijuana, cocaine, heroin, tobacco, sugar, coffee and colas" after "addicts".

Signed and Sealed this

Fifteenth Day of November, 1994

Attest:

BRUCE LEHMAN

Attesting Officer

Commissioner of Patents and Trademarks